(12) United States Patent
Orr et al.

(10) Patent No.: US 8,399,671 B2
(45) Date of Patent: Mar. 19, 2013

(54) METHODS FOR PRODUCING HYDROCODONE, HYDROMORPHONE OR A DERIVATIVE THEREOF

(75) Inventors: Brian Orr, O'fallon, MO (US); William E. Dummitt, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 233 days.

(21) Appl. No.: 12/885,851

(22) Filed: Sep. 20, 2010

(65) Prior Publication Data

US 2011/0071297 A1 Mar. 24, 2011

Related U.S. Application Data

(60) Provisional application No. 61/244,474, filed on Sep. 22, 2009.

(51) Int. Cl.
  *C07D 489/02* (2006.01)
  *C07D 489/00* (2006.01)
(52) U.S. Cl. .......................................... 546/45; 546/44
(58) Field of Classification Search .................... 546/45, 546/44
See application file for complete search history.

(56) References Cited

U.S. PATENT DOCUMENTS

| 3,812,132 A | 5/1974 | Grew et al. |
| 2006/0009479 A1 | 1/2006 | Bailey et al. |

OTHER PUBLICATIONS

Pasto et al., "Reduction with Diimide", Organic Reactions, 1991, 40, pp. 91-155, XP 009067101.
Carroll et al., "One-Pot Conversion of Thebaine to Hydrodocone and Synthesis of Neopinone Ketal", J. Org. Chem., 2009, 74, pp. 747-752.
Leisch et al., "Studies on regioselective hydrogenation of thebaine and its conversion to hydrocodone", Tetrahedron Letters, 2007, 48, pp. 3979-3981.
Small, "Chemistry of the Opium Alkaloids", Public Health Reports, Supplement No. 103, 1932, pp. 252.

*Primary Examiner* — Charanjit Aulakh

(57) ABSTRACT

The present disclosure generally relates to methods for producing opioid derivatives. More particularly, the present disclosure relates to the preparation of hydromorphone, hydrocodone, or a derivative thereof, by means of a non-catalytic hydrogenation reaction of thebaine, oripavine or a derivative thereof, respectively, using a hydrazide reagent, followed by hydrolysis of the hydrogenated intermediate at a low temperature and for a short period of time. Additionally, the present disclosure relates to a composition comprising the desired hydromorphone, hydrocodone, or a derivative thereof, in combination with a 6-beta compound that is structurally related thereto.

12 Claims, 1 Drawing Sheet

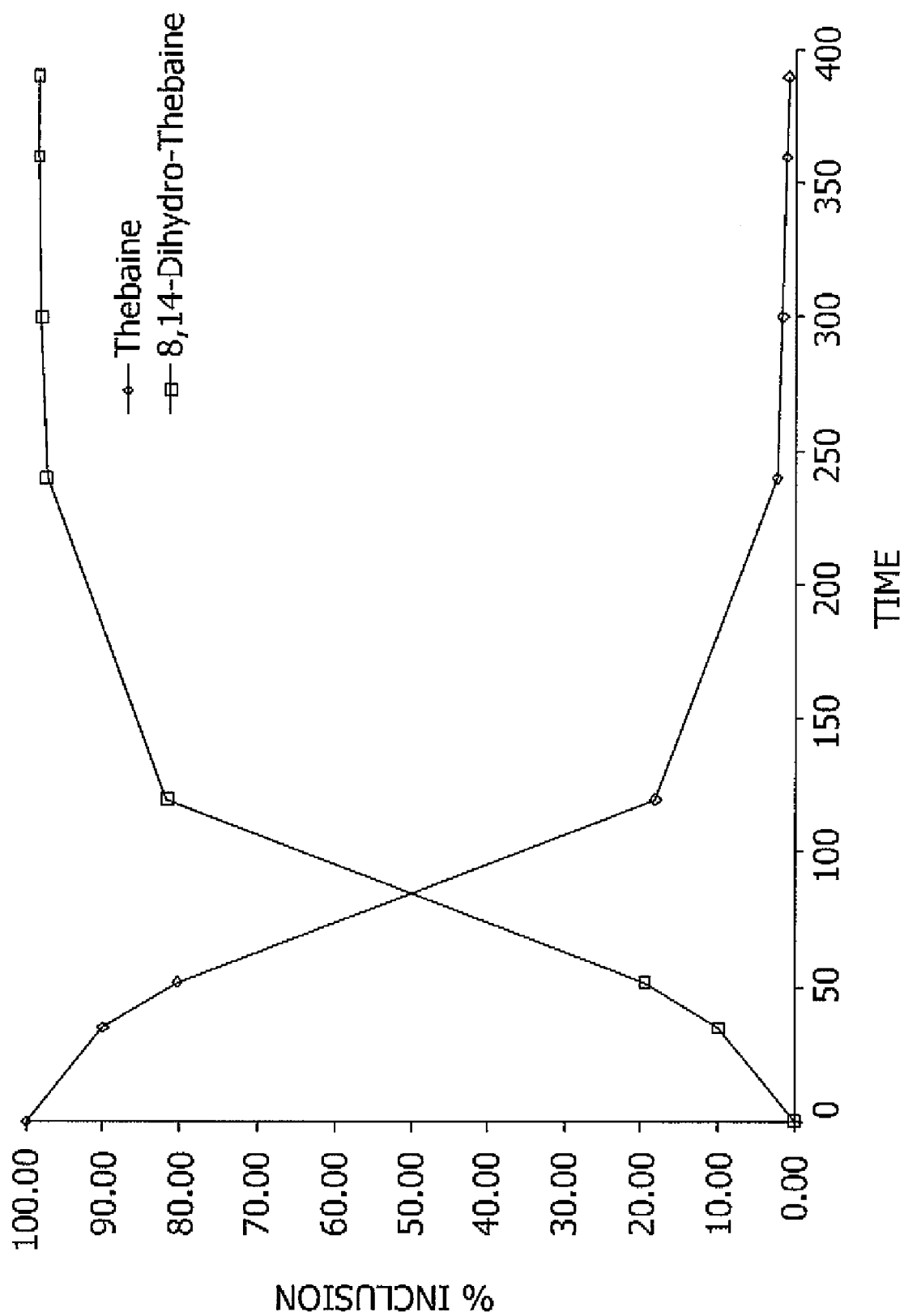

METHODS FOR PRODUCING HYDROCODONE, HYDROMORPHONE OR A DERIVATIVE THEREOF

CROSS-REFERENCE TO RELATED APPLICATION

This application claims priority to U.S. Provisional Patent Application Ser. No. 61/244,474, filed on Sep. 22, 2009, the entire content of which is incorporated herein by reference.

BACKGROUND OF THE DISCLOSURE

The present disclosure generally relates to methods for producing opioid derivatives. More particularly, the present disclosure relates to the preparation of hydromorphone, hydrocodone, or a derivative thereof, by means of a non-catalytic hydrogenation reaction of thebaine, oripavine or a derivative thereof, respectively, using a hydrazide reagent, followed by hydrolysis of the hydrogenated intermediate at a low temperature and for a short period of time. Additionally, the present disclosure relates to a composition comprising the desired hydromorphone, hydrocodone, or a derivative thereof, in combination with a 6-beta compound that is structurally related thereto.

Hydrocodone and hydromorphone are opiate analgesics having similar properties to codeine and morphine. The development of new opiate derivatives are desirable as potential sources of new analgesics. Conventional methods for producing hydrocodone and hydromorphone typically involve a two or three step process, involving reductions/oxidations, usually from morphine or codeine. Unfortunately, the latter methods can be expensive and inefficient.

Attempts to improve efficiency have included the use of catalytic methods. Known catalytic methods include the use of metallic catalysts or complexes, deposited on a support of some kind (e.g., an activated carbon support). However, the preparation of the catalysts can be difficult and yields are often poor, and isolation of the product is often burdensome. Furthermore, morphine and codeine are themselves intrinsically valuable analgesics and their use as reaction starting compounds limits them from being used for medicinal purposes in their own right.

Known catalytic methods, including the use of finely-divided platinum or palladium in an acidic media, can be environmentally undesirable. Enzymatic methods of conversion have also been attempted. However, like many of the catalysts discussed above, they can be costly and difficult to scale up.

Accordingly, a need continues to exist for improved methods for producing various opioids, including hydrocodone, hydromorphone, and derivatives thereof. Desirably, such methods would not require use of heterogeneous or homogeneous metal catalysts and/or would not utilize morphine or codeine as starting compounds.

SUMMARY OF THE DISCLOSURE

In view of the foregoing, the present disclosure is directed, in one embodiment, to a method for preparing a compound of Formula III from a compound of Formula I:

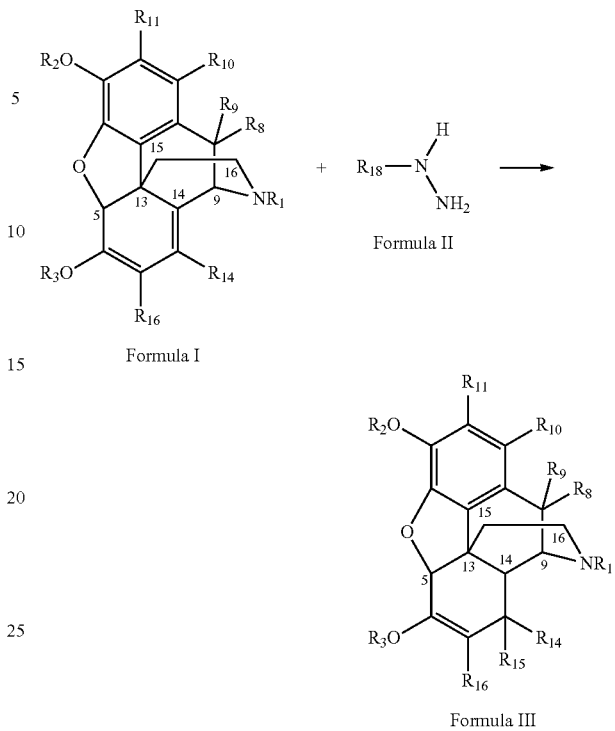

The method comprising contacting the compound of Formula I and a hydrazide reagent of Formula II in a first reaction mixture for at least 6 hours, to convert the compound of Formula I to the compound of Formula III, wherein: $R_1$ is selected from the group consisting of hydrogen, substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester, and substituted or unsubstituted carboxyamide; $R_2$ is selected from hydrogen, substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_3$ is selected from substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_8$ and $R_9$ are independently selected from the group consisting of hydrogen, hydroxyl, and substituted or unsubstituted hydrocarbyl, or $R_8$ and $R_9$ together form a carbonyl group; $R_{10}$, $R_{11}$, $R_{14}$ and $R_{15}$ are independently selected from the group consisting of hydrogen, substituted and unsubstituted hydrocarbyl, and a halogen, or $R_{14}$ and $R_{15}$ together form a carbonyl group; $R_{18}$ is selected from the group consisting of hydrogen, and substituted or unsubstituted hydrocarbyl; and, $R_{18}$ is either an acyl group having the formula $R_{19}$—C(O)— or a sulfonyl group having the formula $R_{20}$—S(O)$_2$—, wherein $R_{19}$ and $R_{20}$ are independently selected from H, substituted or unsubstituted alkyl, substituted or unsubstituted aryl, substituted or unsubstituted aryl alkyl, substituted or unsubstituted cycloalkyl, substituted or unsubstituted heterocycloalkyl, and substituted or unsubstituted heteroaryl. In particular, the present disclosure is directed to such a method wherein a catalyst is not used; that is, the present disclosure is directed to such a method that is non-catalytic.

In another embodiment, the present disclosure is directed to the foregoing method, the method additionally comprising preparing the compound of Formula VI from the compound of Formula III:

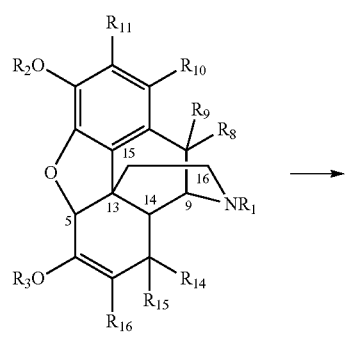

Formula III

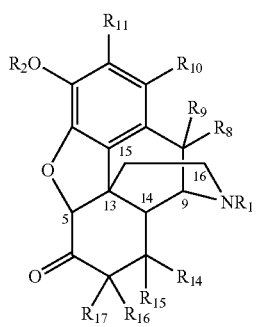

Formula VI

This method comprises contacting the compound of Formula III and an acid in a second reaction mixture at a temperature of less than 50° C., to convert the compound of Formula III to the compound of Formula IV, wherein: $R_1$, $R_2$, $R_3$, $R_8$, $R_9$, $R_{10}$, $R_{11}$, $R_{14}$, $R_{15}$, $R_{16}$ are as previously defined above, and $R_{17}$ is hydrogen.

In yet another embodiment, the present disclosure is directed to a method for preparing a compound of Formula VI:

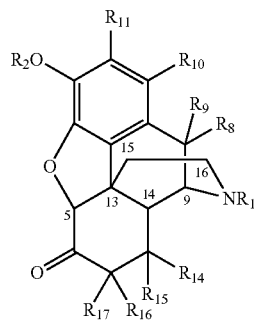

Formula VI wherein: $R_1$ is selected from the group consisting of hydrogen, substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester, and substituted or unsubstituted carboxyamide; $R_2$ is selected from the group consisting of hydrogen, substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_8$ and $R_9$ are independently selected from the group consisting of hydrogen, hydroxyl, and substituted or unsubstituted hydrocarbyl, or $R_3$ and $R_9$ together form a carbonyl group; $R_{10}$, $R_{11}$, $R_{14}$ and $R_{15}$ are independently selected from the group consisting of hydrogen, substituted and unsubstituted hydrocarbyl, and a halogen, or $R_{14}$ and $R_{15}$ together form a carbonyl group; $R_{18}$ is selected from the group consisting of hydrogen, and substituted or unsubstituted hydrocarbyl and $R_{17}$ is hydrogen. The method comprises: (i) contacting a compound of Formula I and a hydrazide reagent of Formula II in a first reaction mixture for a first reaction time of at least 6 hours to form a compound of Formula III:

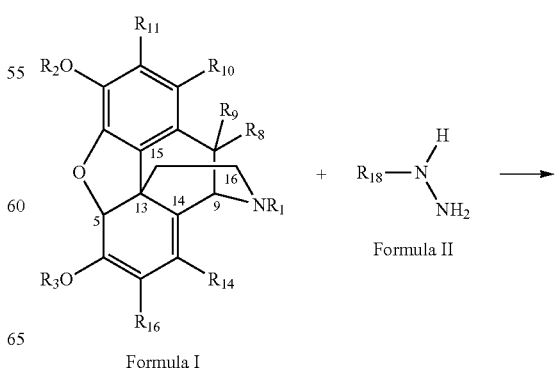

Formula I    Formula II

-continued

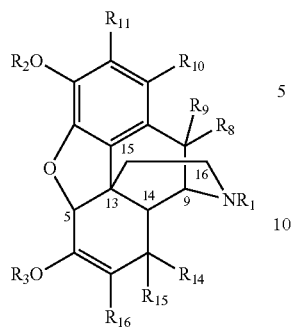

Formula III wherein: $R_1$, $R_2$, $R_8$, $R_9$, $R_{10}$, $R_{11}$, $R_{14}$, $R_{15}$, $R_{16}$ are as previously defined; $R_3$ is selected from the group consisting of substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl and $R_{18}$ is either an acyl group having the formula $R_{19}$—C(O)— or a sulfonyl group having the formula $R_{20}$—S(O)$_2$—, wherein $R_{10}$ and $R_{20}$ are independently selected from H, substituted or unsubstituted alkyl, substituted or unsubstituted aryl, substituted or unsubstituted aryl alkyl, substituted or unsubstituted cycloalkyl, substituted or unsubstituted heterocycloalkyl, and substituted or unsubstituted heteroaryl; and, (ii) contacting the first reaction mixture after the first reaction time with an acid to form a second reaction mixture at a temperature of less than 50° C., to form the compound of Formula VI. In particular, the present disclosure is directed to such a method wherein a catalyst is not used in the reaction to form the compound of Formula III; that is, the present disclosure is directed to such a method wherein the compound of Formula III is formed by a non-catalytic reaction.

In yet another embodiment, the present disclosure is directed to a method for preparing a compound of Formula IV from a compound of Formula III:

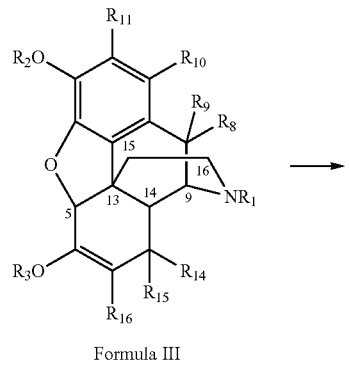

Formula III

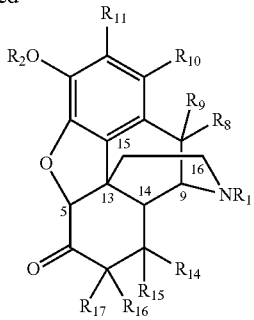

Formula VI wherein: $R_1$ is selected from the group consisting of hydrogen, substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester, and substituted or unsubstituted carboxyamide; $R_2$ is selected from the group consisting of hydrogen, substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_3$ is selected from the group consisting of substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_8$ and $R_9$ are independently selected from the group consisting of hydrogen, hydroxyl, and substituted or unsubstituted hydrocarbyl, or $R_8$ and $R_9$ together form a carbonyl group; $R_{10}$, $R_{11}$, $R_{14}$ and $R_{15}$ are independently selected from the group consisting of hydrogen, substituted and unsubstituted hydrocarbyl, and a halogen, or $R_{14}$ and $R_{15}$ together form a carbonyl group; $R_{16}$ is selected from the group consisting of hydrogen, and substituted or unsubstituted hydrocarbyl; and, $R_{17}$ is hydrogen. The method comprises contacting the compound of Formula III and an acid in a reaction mixture at a temperature of less than 50° C., to convert the compound of Formula III to the compound of Formula VI.

In yet another embodiment, the present disclosure is directed to a compound having a Formula 6-beta below:

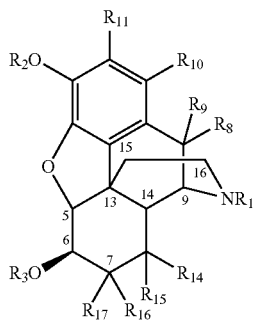

6-beta wherein: $R_1$, $R_2$, $R_3$, $R_8$, $R_9$, $R_{10}$, $R_{11}$, $R_{14}$, $R_{15}$, $R_{16}$ and $R_{17}$ are as previously defined.

In yet another embodiment, the present disclosure is directed to a composition comprising the compound of Formula VI and the structurally related compound of Formula 6-beta, as illustrated previously.

In yet another embodiment, one or more of the above-described processes additionally comprises a recrystallization step in order to remove the previously described 6-beta compound from the structurally related compound of Formula VI, the structurally related compound of Formula III, or both.

It is to be noted that one or more of the additional features detailed below may be incorporated into one or more of the above-noted embodiments, without departing from the scope of the present disclosure.

BRIEF DESCRIPTION OF THE DRAWINGS

FIG. 1 is a graphical illustration of the kinetic profile of hydrogenation of thebaine to 8,14-dihydro-thebaine, according to Example 1.

DETAILED DESCRIPTION OF THE DISCLOSURE

In accordance with the present disclosure, it has been discovered that hydrazide reagents may be used to hydrogenate thebaine, oripavine and their derivatives to produce a hydrogenated intermediate, which may in turn be hydrolyzed to produce hydromorphone, hydrocodone, or a derivative thereof, respectively. The hydrogenation reaction is non-catalytic, and has been found to provide a more complete reaction, or provide a reaction product in higher yield, if the reaction is allowed to proceed for at least 6 hours, which considerably longer than previously disclosed. (See, e.g., U.S. Pat. No. 3,812,132 and U.S. Patent Application Publication No. 2006/0009479, the entire contents of which are incorporated herein by reference for all relevant and consistent purposes). It has been further discovered that, once formed, the hydrogenated intermediate may be simply recovered from the reaction by dilution, cooling and filtering, rather than by a conventional solvent evaporation followed by an extraction process. Furthermore, hydrolysis of the intermediate has been found to approach completion in a relatively short period of time and without extraneous addition or application of heat to the reaction mixture; that is, the hydrolysis reaction has been found to occur at low temperatures (e.g., at about room temperature) and within a few hours (e.g., about 2 hours or less). The avoidance of heating minimizes impurity and color formation in the product.

In this regard it is to be noted that, as used herein, "non-catalytic" or "non-catalyzed" refers to a reaction in which a conventional or known catalyst, and more specifically a conventional or known metal-containing catalyst, is not used to aid the reaction and is not present in the reaction mixture.

As noted, the methods described herein result in high conversion of the starting material or compound to the analgesic product without significant input of heat into the reaction mixture. As an illustration, and therefore not to be viewed in a limiting sense, in various embodiments a conversion of about 85 mole %, about 90 mole %, about 95 mole %, about 99 mole % or more may be achieved in accordance with the methods of the present disclosure, ultimately leading to a compound having a purity of about 90 wt %, at least about 95 wt %, about 99 wt % or more (as determined by means generally known in the art).

1. Opioid Starting Materials and Hydrogenated Intermediates

In one embodiment of the non-catalytic method of present disclosure, a compound of Formula III may be prepared by contacting a compound of Formula I with a hydrazide reagent:

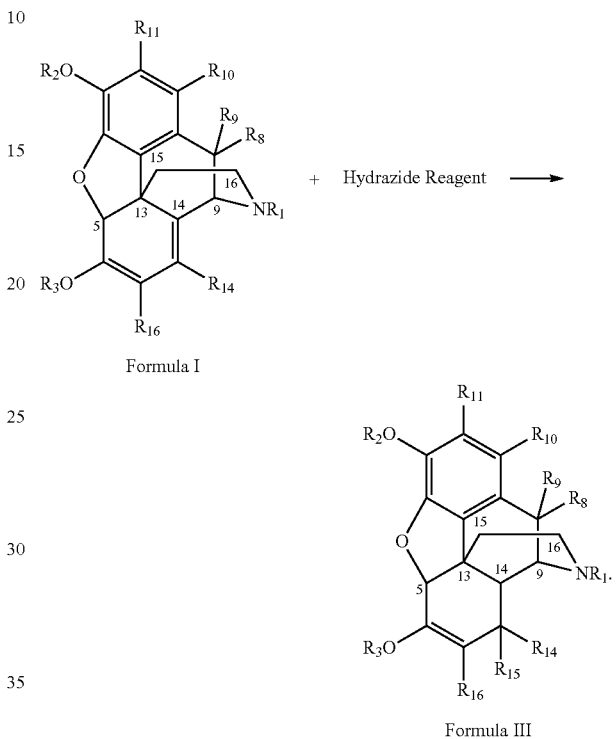

In the structures, $R_1$ may be selected from, for example, hydrogen, substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester, and substituted or unsubstituted carboxyamide. Additionally, $R_2$ may be selected from hydrogen, substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_3$ may be selected from substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl; $R_8$ and $R_9$ may be independently selected from the group consisting of hydrogen, hydroxyl, substituted or unsubstituted hydrocarbyl. Alternatively, $R_8$ and $R_9$ may together form a carbonyl group. $R_{10}$, $R_{11}$, $R_{14}$ and $R_{15}$ may independently be selected from the group consisting of hydrogen, substituted and unsubstituted hydrocarbyl, and a halogen. Alternatively, $R_{14}$ and $R_{15}$ may together form a carbonyl group. $R_{16}$ may independently be selected from the group consisting of hydrogen, hydrocarbyl and substituted hydrocarbyl.

In some embodiments of the present disclosure, $R_1$ may be selected from the group consisting of hydrogen, and —OCOR$_4$, and $R_4$ may be selected from the group consisting of hydrocarbyl and substituted hydrocarbyl. In such embodiments, $R_2$ may be selected from the group consisting of hydrogen, and methyl.

In several particular embodiments, $R_1$ and $R_3$ are methyl and $R_2$ is methyl or hydrogen. In such embodiments, all other R groups (i.e., $R_8$, $R_9$, $R_{10}$, $R_{11}$, $R_{14}$, $R_{15}$, and $R_{16}$) may be hydrogen; that is, Formula I may be thebaine or oripavine, respectively, leading to the formation of 8,14-dihydro-thebaine or 8,14-dihydro-oripavine, respectively. Stated differently, the non-catalytic reaction may be carried out to convert a compound of Formula IA to a compound of Formula IIIA, or it may be carried out to convert a compound of Formula IB to a compound of Formula IIIB, as illustrated below:

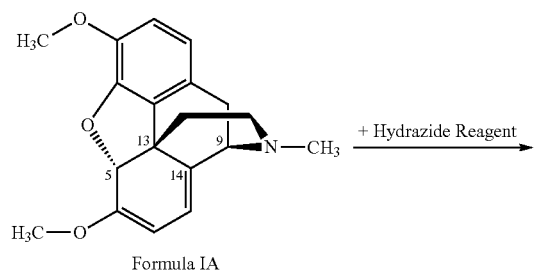

Formula IA

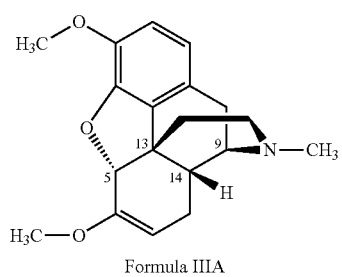

Formula IIIA

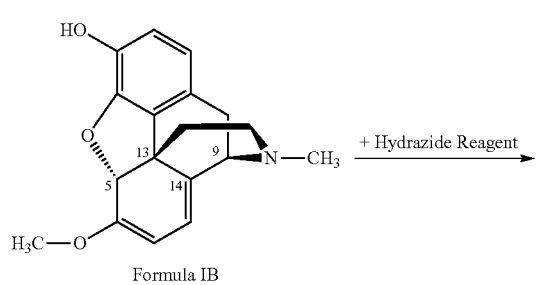

Formula IB

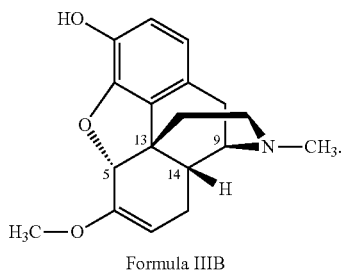

Formula IIIB

In certain embodiments, the compounds of Formula I and III may be in the stereochemical form of the (+)-enantiomer. In such embodiments, the stereochemistry of the C(5), C(13), and C(9) carbons for Formula I and C(5), C(13), C(14) and C(9) for Formula III, respectively, of each compound may be selected from the group consisting of a combination listed in Table A, below (wherein the C(5), C(13), C(14), and C(9) carbon atoms are noted in the structures of Formulas I and III, above). In such structures, the C(15) and the C(16) atoms are for stereo-chemical reasons connected and on the same face, but may be either on the alpha face or the beta face of the molecule.

TABLE A

Stereoisometric combinations for C(5), C(13) and C(9) carbons of Formula I and C(5), C(13), C(14) and C(9) for Formula III respectively.

| Combination | C5 | C13 | C14 | C9 |
|---|---|---|---|---|
| 1 | R | R | R | R |
| 2 | R | R | S | R |
| 3 | R | R | R | S |
| 4 | R | R | S | S |
| 5 | R | S | R | R |
| 6 | R | S | S | R |
| 7 | R | S | R | S |
| 8 | R | S | S | S |
| 9 | S | R | R | R |
| 10 | S | R | S | R |
| 11 | S | R | R | S |
| 12 | S | R | S | S |
| 13 | S | S | R | R |
| 14 | S | S | S | R |
| 15 | S | S | R | S |
| 16 | S | S | S | S |

In this regard it is to be noted that the stereochemical configurations in Table A should not be viewed in a limiting sense. For example, depending on the exact composition of the molecule, it may not be possible to form one or more of the above-noted stereochemical configurations (i.e., the stereochemical limitations of the molecule may not allow for one or more of the noted configurations to be formed).

In an alternative embodiment of the present disclosure, the reactant or starting compounds and/or reaction products may be in the form quaternary amine (or ammonium) salts. For example, in such an embodiment, a compound of Formula IV may be contacted with a hydrazide reagent in a hydrogenation reaction to produce a compound of Formula V:

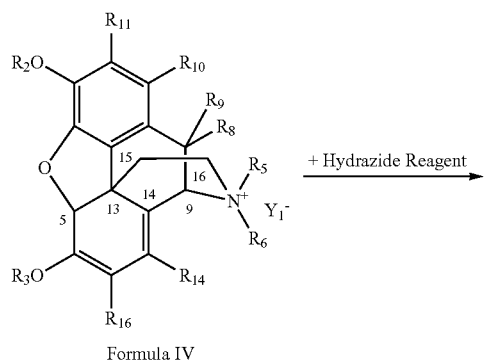

Formula IV

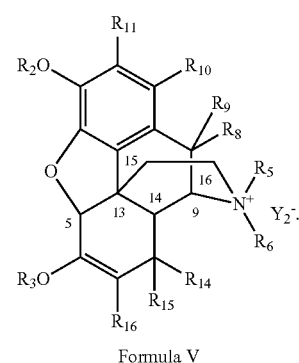

Formula V

In the structures, $R_2$, $R_3$, $R_8$-$R_{11}$ and $R_{14}$-$R_{16}$ are as defined above, while $R_5$ and $R_6$ may be, for example, independently selected from hydrogen, substituted or unsubstituted alkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester and substituted or unsubstituted carboxyamide. $Y_1$ and $Y_2$ are anions, each independently selected from, for example, a halogen ion (e.g., Cl$^-$, F$^-$, Br$^-$, I$^-$), as well as $BF_4^-$, $ClO_4^-$, $HCO_2^-$, $CF_3CO_2^-$, $CF_3SO_3^-$, $CH_3CO_2^-$, $ArCO_2^-$, $CH_3SO_3^-$, p-tolylSO$_3^-$, HSO$_4$ and $H_2PO_4^-$. It is to be noted that $Y_1$ and $Y_2$ may be the same or different.

It is to be further noted that while the starting compounds and hydrogenated intermediate compounds illustrated above have the same base or core structure (i.e., a fused, tetracyclic structure), the methods of the present disclosure may be used with other compounds having similar functionalities. Additionally, or alternatively, it is to be noted that, like the structures of Formulas I and II, the process of the present disclosure may be used to prepare the (+)-enantiomers of Formulas IV and V, above.

While the base or core structure of the compounds illustrated above has a specific arrangement of substituents, additional substituents and/or different substituents may be present at one or more sites therein without departing from the scope of the present disclosure, provided the substituted structure remains an alkaloid having similar functionality. Accordingly, the structures illustrated in, for example, Formulas I through V above should not be viewed in a limiting sense.

It is also to be noted that the starting compounds referenced herein, such as those of Formula I and Formula IV, and in particular the compounds of Formula IA and Formula IB, may be obtained commercially, and/or may be prepared according to methods generally known in the art.

2. Hydrazide Reagent

As previously noted, the hydrogenation reaction may be achieved without the aid of a catalyst (e.g., a conventional metal catalyst). Rather, a hydrazide reagent is used. The hydrazide reagent contacted with a starting compound described above (e.g., a compound of Formula I, IA, IB or IV) may have the structure of Formula II, below:

Formula II

In the structure, $R_{18}$ may be either an acyl group having the formula $R_{19}$—C(O)— or a sulfonyl group having the formula $R_{20}$—S(O)$_2$—, wherein $R_{19}$ and $R_{20}$ are independently selected from hydrogen substituted or unsubstituted alkyl, substituted or unsubstituted aryl, substituted or unsubstituted aryl alkyl, substituted or unsubstituted cycloalkyl, substituted or unsubstituted heterocycloalkyl and substituted or unsubstituted heteroaryl.

In some embodiments, $R_{18}$ is a sulfonyl group having the formula $R_{20}$—S(O)$_2$—, wherein $R_{20}$ is substituted or unsubstituted aryl having one or more rings, each ring having 5 or 6 atoms. One or more of the atoms therein may optionally be a heteroatom, such as O, N and S. In various particular embodiments, $R_{20}$ may be a phenyl, bi-phenyl or alkylphenyl group. In certain preferred embodiments, however, $R_{20}$ is tolyl; that is, the hydrazide reagent is p-toluene sulphonyl hydrazide. The hydrazide reagent may in another preferred embodiment be 2,4,6-triisopropylbenzene sulphonyl hydrazide.

3. Hydrogenation Reaction

The non-catalytic hydrogenation reaction may be performed according to methods generally known in the art, which involve contacting a starting compound as detailed herein (i.e., a compound of Formula I, IA, IB or Formula IV) with a hydrazide reagent (i.e., a compound of Formula II). An exemplary method includes contacting (e.g., dissolving or suspending) the starting compound in a suitable solvent in a reaction vessel. Suitable solvents may be selected from, for example, 2-methoxy-ethanol, ethanol amine, 2-ethoxy-ethanol, ethanol, isopropanol, 1-butanol, 2-butanol, dimethylene glycol dimethyl ether, ditheylene glycol dimethyl ether, toluene, water, dimethyl sulfoxide, N,N-dimethyl formamide, dioxane and methyl t-butyl ether, as well as combinations thereof. Generally, the reaction proceeds to completion in one step; stated differently, compounds of Formula III, IIIA, IIIB, and Formula V are produced from compounds of Formula I, IA, IB and Formula IV without formation and/or isolation of intermediate compounds.

The reaction vessel may be flushed with an inert atmosphere, such as argon or nitrogen, prior to beginning the reaction. However, the reaction may additionally proceed with suitable conversion under an ambient atmosphere (i.e., under air). The reaction mixture may be refluxed, optionally under the inert atmosphere, until the hydrogenation reaction (or conversion) is essentially complete (as determined using means generally known in the art, such as for example UPLC or TLC, to analyze or measure the concentration of the desired reaction product, and/or the starting compound, in the reaction mixture). The reaction vessel may be maintained at atmospheric pressure; however, other pressures may be used without limitation.

It has been found that suitable conversion to compounds of Formula III, IIIA, IIIB, and V may be achieved when the starting compounds (i.e., compounds of Formula I, IA, IB and IV, respectively) are contacted with the hydrazide reagent for about 6 hours, about 6.5 hours, about 7 hours, about 7.5 hours, or even about 8 hours or more. Optionally, the compounds may be contacted for less than 24 hours (e.g., about 20 hours, about 18 hours, about 16 hours, about 14 hours, about 12 hours, or about 10 hours, or less). Accordingly, in various embodiments the two compounds may be contacted or reacted for a duration of between about 6 hours and 24 hours, or about 7 hours and about 18 hours, or about 8 hours and about 14 hours. In these or other embodiments, the conversion to the hydrogenated intermediate (i.e., compounds of Formula III, IIIA, IIIB, or V) may be about 85 mole %, about 90 mole %, about 95 mole % or even about 99 mole % or more (as determined by means generally known in the art), after isolation and purification of the reaction product (using means generally known in the art).

In certain embodiments, the hydrazide reagent and opioid starting compounds are added to the first reaction mixture in an amount such that the compound of Formula II and the compound of Formula I are present in the reaction mixture in a ratio of about 1:1 or, in other embodiments, about 1.5:1, about 2:1, about 2.5:1 or even about 3:1 or more. Singly or in combination with these embodiments, the first reaction mixture may contain the compound of Formula II and the compound of Formula I in a ratio of about 6:1, about 5.5:1, about 5:1, about 4.5:1, about 4:1, or less, the ratio therefore being within a range of, for example, about 1:1 and about 6:1, or about 1.5:1 and about 5:1, or about 2:1 and about 4:1. In one particular embodiment, however, the method of the present disclosure utilizes a first reaction mixture containing the compound of Formula II and the compound of Formula I in a ratio of greater than about 2:1 and less than about 3:1, with a ratio of about 2.2:1 being preferred.

In this regard it is to be noted, however, that the ratio of starting materials may be altered as needed in order to optimize yield or conversion, and/or purity, of the desired reaction product. Accordingly, the ranges provided herein are for illustration, and therefore should not be viewed in a limiting sense.

In these or yet other alternative embodiments, the reaction mixture may be maintained at a temperature of greater than about 60° C. and a temperature below that at which the hydrazide reagent begins to decompose (e.g., a temperature of less than 110° C.), or between about 70° C. and about 105° C., or about 80° C. and about 100° C., with higher temperatures typically being used in combination with shorter reaction (or contact) times, as detailed above.

In this regard it is to be noted that, in one particular embodiment, the hydrazide reagent, the starting compound (e.g., the compound of Formula I, IA, IB or IV), and the solvent are combined to form the reaction mixture in a reaction vessel, and then the resulting mixture is heated to the desired temperature for the desired time, in order to carry out the reaction as detailed herein.

After the reaction has reached a desired point of completion (determined as noted above), the mixture may be cooled as needed and the hydrogenated intermediate (e.g., compounds of Formula III, IIIA, IIIB, or V) may be isolated using methods generally known in the art (e.g., filtration, centrifugation, crystallization, chromatography, etc.). For instance, the first reaction mixture may be cooled to about room temperature or lower (e.g., less than about 20° C., about 15° C., about 10° C., or about 5° C.) to cause the hydrogenated intermediate to crystallize. Upon crystallization and dilution, the hydrogenated intermediate may be filtered from the reaction mixture. Once isolated, the reaction product may be further purified if needed, again using methods generally known in the art (e.g., purified by recrystallization in a suitable solvent as is well known in the art, or by any other conventional methods of purification, such as chromatography), and/or as further detailed herein below.

4. Hydrolysis Reaction

Upon formation of the hydrogenated intermediate compounds (compounds of Formula III, IIIA, IIIB, or V), the compounds may be contacted with an acid to produce a compound of Formula VI as shown below:

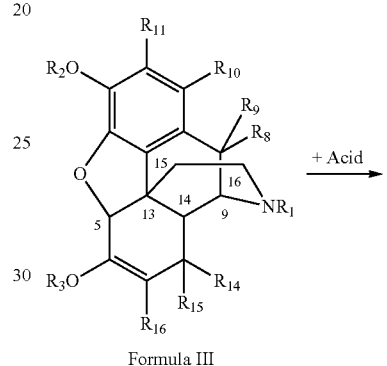

Formula III

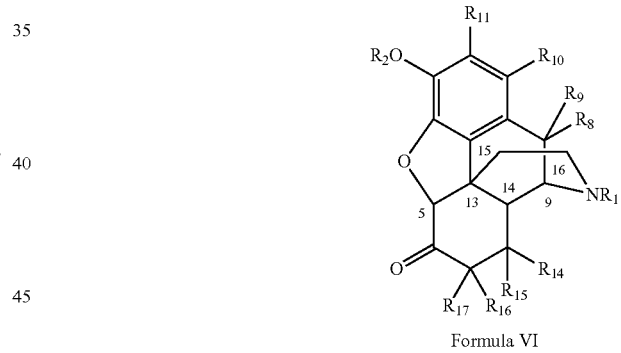

Formula VI wherein: $R_1$, $R_2$, $R_3$, $R_8$, $R_9$, $R_{10}$, $R_{11}$, $R_{14}$, $R_{15}$ and $R_{16}$ are defined as above. In the structure of Formula VI, $R_{17}$ is hydrogen. Exemplary methods include contacting Formula III and the acid in a reaction mixture (referred to herein as a "second" reaction mixture, the reaction mixture for the hydrogenation reaction detailed above being the first) and allowing the reaction to proceed to the desired completion. Suitable acids include, for example, hydrochloric acid, sulfuric acid, hydrobromic acid, hydro-iodic acid, trifluoro acetic acid, acetic acid and phosphoric acid. The acid may be included in an aqueous solution and the concentration of the acid therein may be between about 1 normal (N) and about 12N, or between about 2N and about 10N, or between about 2.5N and about 6N. In some embodiments, the acid (e.g., sulfuric acid)

concentration in the aqueous solution may be between about 1 molar (M) and about 5M, or between about 1.5M and about 3M.

As stated above, in several particular embodiments, $R_1$ and $R_3$ are methyl and $R_2$ is methyl or hydrogen. In such embodiments, all other R groups (i.e., $R_8$, $R_9$, $R_{10}$, $R_{11}$, $R_{14}$, $R_{15}$, $R_{16}$, $R_{17}$) may be hydrogen; that is, the reaction may lead to formation of hydrocodone or hydromorphone, respectively, as illustrated below:

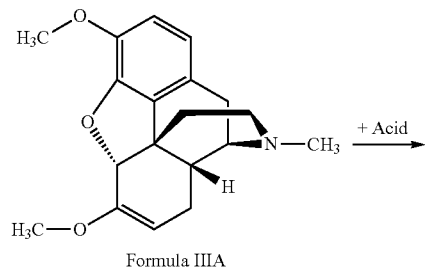

Formula IIIA

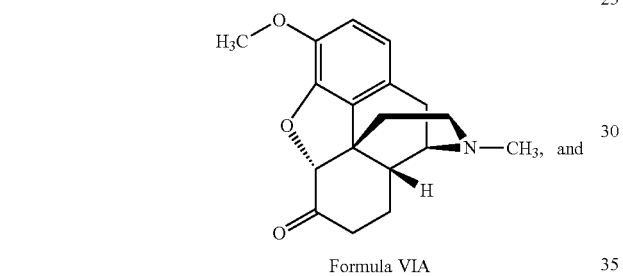

Formula VIA

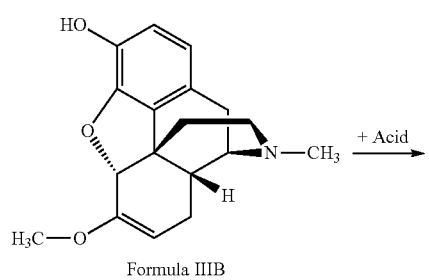

Formula IIIB

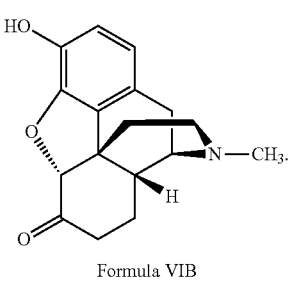

Formula VIB

It is to be noted that the compounds of Formula III and VI may be (+)-enantiomers as described above, with the stereochemistry of the atoms being selected from the combinations shown in Table A, above. It is to be further noted that the hydrogenated intermediate (including the (+)-enantiomer thereof) may optionally be a quaternary amine (or ammonium salt), such as compound V, the reaction proceeding as illustrated below:

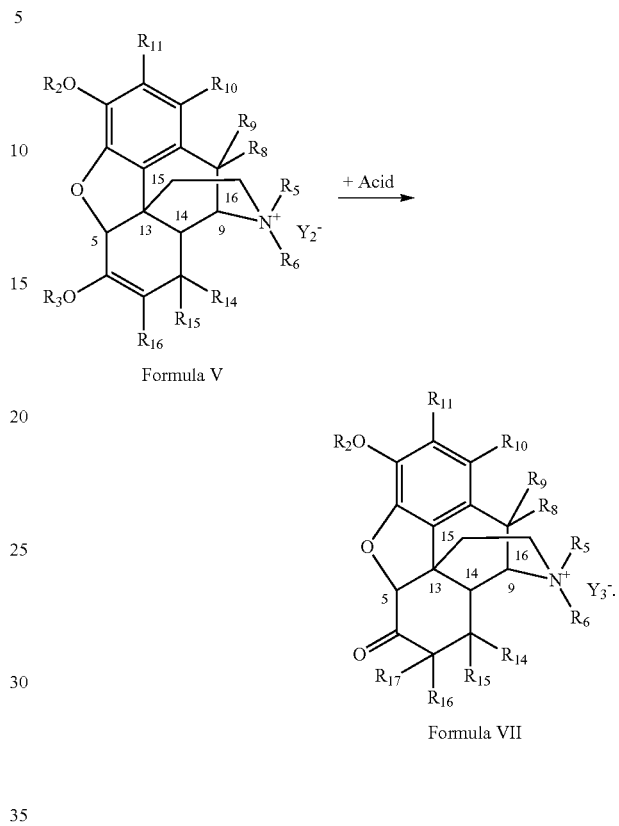

Formula V

Formula VII

In the structures of Formulas V and VII, above, $R_2$, $R_3$, $R_5$, $R_6$, $R_8$-$R_{11}$, $R_{14}$-$R_{17}$ and $Y_2$ are as defined above. Additionally, $Y_3$ may be an anion selected from, for example, a halogen ion (e.g., $Cl^-$, $F^-$, $Br^-$, $I^-$), as well as $BF_4^-$, $PF_6^-$, $ClO_4^-$, $HCO_2^-$, $CF_3CO_2^-$, $CF_3SO_3^-$, $CH_3CO_2^-$, $ArCO_3^-$, $CH_3SO_3^-$, p-tolylSO$_3^-$, $HSO_4^-$ and $H_2PO_4^-$. $Y_2$ and $Y_3$ may be the same or different. In embodiments wherein a compound of Formula VII is produced, the Formula VII compound is isolated by neutralization of the acid reaction with a suitable base (e.g., ammonium hydroxide or sodium hydroxide) to provide the free base opiate thereof.

It is to be noted that while the hydrogenated intermediate compounds and hydrolysis reaction product compounds illustrated above have the same base or core structure (i.e., a fused, tetracyclic structure), the methods of the present disclosure may be used with other alkaloids having similar functionalities. Additionally, or alternatively, it is to be noted that, like the structures of Formulas III and VI, the process of the present disclosure may be used to prepare the (+)-enantiomers of Formulas V and VII, above. Accordingly, the structures illustrated in, for example, Formulas VI, VIA, VIB and VII should not be viewed in a limiting sense.

It has been found that the hydrogenated intermediate may be converted to the hydrolysis product with high conversion (e.g., about 85 mole %, about 90 mole/0, about 95 mole % or even about 99 mole % or more) with little or no addition of extraneous heat to the second reaction mixture, Further, it has been found conversion at relatively low temperatures generally leads to formation of fewer by-products (see, e.g., Example 2) and minimizes color formation. Accordingly, the second reaction mixture may be maintained (i.e., the reaction may be carried out) for a desired period of time at a temperature of about 50° C., about 40° C., about 30° C., about 20° C., or even less (the temperature for example being between about 50° C. and about 20° C., or between about 40° C. and about 30° C.). In one particular embodiment, however, the second reaction mixture maintained at about room temperature (i.e., the reaction is carried out at about room temperature) for a desired period of time. Although the reaction times may vary, optionally or additionally, the hydrogenated intermediate may be contacted with the acid in the second reaction mixture for less than about 24 hours, about 18 hours, about 12 hours, about 6 hours, about 3 hours, or even about 2 hours, while the minimum reaction time may be about 0.5 hours, about 1 hour, about 1.5 hours or more (the duration of the reaction thus being, for example, between about 0.5 hours and about 3 hour, or between about 1 hour and about 2 hours).

In this regard it should be noted, however, that other contact or reaction times and/or temperatures may be used without departing from the scope of the present disclosure.

After the reaction has reached a desired point of completion (determined as noted above), the hydrolysis product (compounds of Formulas VI, VIA, VIB and VII) may be isolated and/or purified by methods known in the art (e.g., filtration, centrifugation, crystallization, chromatography, etc.) to recover the product and to improve its color (i.e., to prepare a product that is substantially white). For instance, the second reaction mixture may be contacted with carbon, activated carbon, diatomaceous earth or a mixture thereof to remove any by-products and/or color. Once isolated, the reaction product may be further purified if needed, again using methods generally known in the art, and/or as further detailed herein below, in order to obtain a final reaction product. In one preferred embodiment, the final reaction product is white, or substantially white, in appearance, the recrystallization providing material that has a concentration of known impurities of about 0.2 wt %, about 0.15 wt %, or even about 0.1 wt %, or less, and/or a concentration of unknown impurities of about 0.1 wt %, about 0.05 wt %, or less.

In this regard it is to be noted that, as part of a final purification step, once isolated from the second reaction mixture, the reaction product may be treated or contacted with charcoal, or a mixture of charcoal and celite, in order to aid with the removal of impurities (including those which impart an undesirable color to the product, giving it for example a brown, beige or grey appearance), the reaction product may is then contacted with a base (e.g., ammonium hydroxide, potassium hydroxide or sodium hydroxide) in order to obtain the free-base form thereof.

It is to be further noted that the hydrogenation and hydrolysis reactions of the present disclosure may be carried out in continuous or batch form and according to any of the methods known by those of ordinary skill in the art.

5. Purification Step

In accordance with the present disclosure, it is to be noted that the compounds illustrated below have been identified as impurities resulting from the initial hydrogenation reaction detailed above (the various substituents noted in the compound structures illustrated below being as previously defined elsewhere herein above):

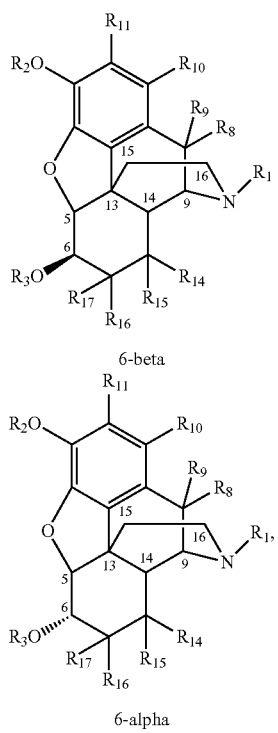

6-beta 6-alpha wherein the various substituents noted therein (i.e., $R_1$, $R_2$, $R_3$, $R_8$, $R_9$, $R_{10}$, $R_{11}$, $R_{14}$, $R_{15}$, $R_{16}$ and $R_{17}$) are as previously defined (and in one or more embodiments $R_{16}$ is selected from the group consisting of substituted or unsubstituted hydrocarbyl). Experience to-date indicates the 6-alpha impurity (e.g., 6-alpha-parzone-methyl ether) is typically soluble in the resulting mixture and readily purged or removed from the desired reaction product (by, for example, filtration to collected the crystallized reaction product there from), at least when present in the resulting mixture at a concentration of about 3 wt % or less. In contrast, the 6-beta impurity (e.g., 6-beta-parzone-methyl ether, or beta-PME) is not so easily removed, due to a difference is solubility. For example, experience to-date indicates that, after filtration and washing of the isolated reaction product, the concentration of the 6-beta impurity therein may be in the range of between about 0.15 wt % and about 0.4 wt % (based on the total, dry weight of the reaction product), as determined by means generally known in the art (e.g., HPLC analysis). If this isolated reaction product is carried forward to the subsequent hydrolysis reaction, experience to-date further indicates that the 6-beta impurity will still be present in the final reaction product (e.g., hydrocodone, hydromorphone, or a derivative thereof), the concentration of the impurity therein being for example between about 0.1 wt % and about 0.3 wt % (based on the total, dry weight of the final reaction product), as determined by means generally known in the art (e.g., HPLC analysis).

Without being held to any particular theory, it is generally believed that formation of the 6-beta impurities occur as a result of the over reduction of compounds of Formula III, or by 1,4-addition of hydrogen to the compounds of Formula I across the 6,14 bonds (i.e., a Diels-Alder type of addition-elimination reaction) followed by the concomitant reduction of the alkene intermediate. Accordingly, it is further believed that the concentration of the 6-beta impurity may be controlled, at least to a limited extent, by control of the molar equivalents of the hydrazide reagent used (the amount thereof preferably being, in various embodiments, about 2.2 equivalents, as detailed elsewhere herein). However, experience to-date also indicates that the level or concentration of the impurity did not increase significantly with increased or excessive hydrazide use (or alternatively reaction time). Again, without being held to a particular theory, it is generally believed that these observations suggest the reaction simply makes a statistical amount of the impurity (or by-product).

In view of the foregoing, it is to be further noted that the present disclosure is additionally directed to a process that includes a purification step following the hydrogenation reaction, the hydrolysis reaction, or both, in order to further reduce or limit the concentration of the 6-beta impurity in the final reaction product. Preferably, the process is carried out to ensure that the concentration of the noted impurity is at or below current the International Conference on Harmonization guidelines (e.g., ICH levels of less than 0.15 wt %, preferably less than 0.125 wt %, or even more preferably less than 0.1 wt %, based on the total, dry weight of the final reaction product), with little or not detrimental impact on yield and/or quality of the final reaction product.

Accordingly, in various preferred embodiments the process of the present disclosure additionally comprises a purification step, and more specifically a recrystallization step, of either the compound of Formula III or Formula VI, or both, to remove the above-noted impurities (and in particular the 6-beta impurity). In one preferred embodiment, however, the impurity (or impurities) is (are) removed by means of the recrystallization of the compound of Formula VI alone. Without being held to any particular theory, recrystallization of the compound of Formula VI alone is preferred, at least in part because it reduces costs and/or the amount of time needed to obtain the desired reaction product. Additionally, experience to-date indicates that recrystallization of a compound of Formula III is typically effective at removing between about 50 wt % and about 65 wt % of the impurity (e.g., 6-beta impurity), while experiencing a yield loss (of the compound of Formula III) of about 10% or less. In contrast, experience to-date further indicates that recrystallization of a compound of Formula VI is typically effective at removing between about 80 wt % and about 95 wt % of the impurity (e.g., 6-beta impurity), while experiencing a similar yield loss (of the compound of Formula III, e.g., about 9 wt % or less). In this regard it is to be noted, however, that experience to-date still further indicates that recycling the filtrate solution (or mother liquor) for (and from) future recrystallization can increase the yield (or decrease the yield loss), such that at least about 94 mol %, 96 mol %, or more, of the desired reaction compound or product is obtained without impact on product quality if the recrystallization is carried out on structures of type Formula VI rather than Formula III.

Recrystallization of the compound of type Formula III, Formula VI, or both, in order to remove the noted impurity may be carried out by means generally known in the art, the conditions thereof being optimized in order to maximize both removal of the impurity and yield of the desired reaction product. In one preferred embodiment, however, the compound to be recrystallized is first dissolved in an appropriate solvent (e.g., an alcohol, such as for example methanol, ethanol, isopropanol, butanol, toluene, isopropyl acetate, ethyl acetate or a mixture thereof, or alternatively an organic solvent such as toluene), the ratio of solvent to the noted compound being, for example, between about 6:1 and about 12:1 (volume solvent to weight of compound), or between about 8:1 and about 10:1. Typically, dissolution is aided or achieved by heating the resulting solution or mixture to an appropriate temperature (e.g., about 75° C. in the case of ethanol, which is preferred in one or more embodiments), the temperature essentially be limited by the boiling point of the solvent, and/or the decomposition temperature of the final product (the temperature being controlled to remain below both). Upon cooling of the solution or mixture, the purified final product will precipitate from the solution for collection.

As noted above, and as further illustrated in Table B (below), experience to-date indicates that the overall yield of the purified final product may be increased (in a continuous, semi-continuous or multi-batch process) if the filtrate solution from recrystallization of compounds of type Formula VI is collected and reused or recycled.

TABLE B

| Re-Cycle | 6-β-PME | Hydrocodone Wt % | Mass Yield |
|---|---|---|---|
| Virgin Crude Isolated Reaction | 0.14 | 98.90 | >95% |
| Crude recrystallization | 0.01 | 99.72 | 90.70 |
| 1$^{st}$ | 0.03 | 99.55 | 96.20 |
| 2$^{nd}$ | 0.03 | 99.69 | 96.00 |
| 3$^{rd}$ | 0.04 | 99.81 | 96.00 |
| 4$^{th}$ | 0.03 | 99.80 | 96.50 |

In view of the foregoing, it is additionally to be noted that, in various embodiments, the present disclosure is further directed to the reduction of the 6-beta compound noted above (wherein each of the noted substituents thereon may generally be as defined elsewhere herein), and in particular is directed to the following compounds:

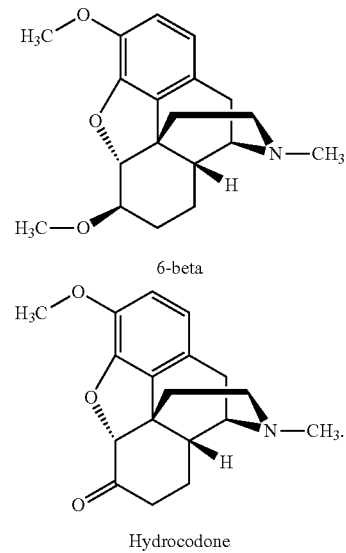

6-beta

Hydrocodone

The present disclosure is still further directed to a purified composition (i.e., a composition having undergone a purification step, such as the one detailed herein above) comprising the combination, or a mixture, of the final, desired compound (i.e., the recrystallized, hydrolysis reaction product) and the structurally related 6-beta compound, both as illustrated above. In various particular embodiments, the present disclosure is directed to a composition comprising greater than 95 wt % (e.g., about 96 wt %, about 97 wt %, about 98 wt % or even about 99 wt %) of the hydrolysis reaction product (based on the total weight of the composition), and less than 100 wt % thereof. Additionally, the composition comprises less than 1 wt % (e.g., about 0.5 wt %, about 0.25 wt %, about 0.15 wt %, or even about 0.1 wt %) of the 6-beta impurity (based on the total weight of the composition), and greater than 0.01 wt %. More particularly, however, the composition typically comprises between about 96 wt % and less than 100 wt %, or between about 98 wt % and less than 100 wt %, of the hydrolysis reaction product (e.g., the compound of Formula VI, and in various embodiments more particularly the recrystallized compound of Formula VIA or VIB), and between about 0.01 wt % and about 0.15 wt %, or between about 0.01 wt % and about 0.1 wt %, or between about 0.01 wt % and about 0.05 wt %, of the structurally related 6-beta compound.

6. Definitions

The compounds described herein may have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present disclosure and intermediates made therein are considered to be part of the present disclosure.

As used herein, "optional" or "optionally" means that the subsequently described event or circumstance may or may not occur, and that the description includes instances where the event or circumstance occurs and instances where it does not.

The terms "aryl" or "ar" as used herein, alone or as part of another group, denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

Unless otherwise indicated, the "alkyl" groups described herein are preferably lower alkyl containing from one to about 10 carbon atoms in the principal chain, and up to about 20 carbon atoms. They may be straight or branched chain or cyclic (e.g., cycloalkyl) and include methyl, ethyl, propyl, isopropyl, butyl, pentyl, hexyl and the like. Accordingly, the phrase "$C_{1-20}$ alkyl" generally refers to alkyl groups having between about 1 and about 20 carbon atoms, and includes such ranges as about 1 to about 15 carbon atoms, about 1 to about 10 carbon atoms, or about 1 to about 5 carbon atoms, while the phrase "$C_{1-10}$ alkyl" generally refers to alkyl groups having between about 1 and about 10 carbon atoms, and includes such ranges as about 1 to about 8 carbon atoms, or about 1 to about 5 carbon atoms.

The term "substituted" as in "substituted aryl" or "substituted alkyl" and the like, means that in the group in question (i.e., the aryl, the alkyl, or other moiety that follows the term), at least one hydrogen atom bound to a nitrogen atom or carbon atom, respectively, is replaced with one or more substituent groups such as hydroxy, alkoxy, amino, halo, and the like. When the term "substituted" introduces a list of possible substituted groups, it is intended that the term apply to every member of that group. That is, the phrase "substituted alkyl, aryl, acyl, etc." is to be interpreted as "substituted alkyl, substituted aryl, and substituted acryl", respectively. Similarly, "optionally substituted alkyl, aryl and acyl" is to be interpreted as "optionally substituted alkyl, optionally substituted aryl and optionally substituted acyl."

The modifiers "hetero", as in "heterocycle" refer to a molecule or molecular fragment in which one or more carbon atoms is replaced with a heteroatom. Thus, for example, the term "heteroalkyl" refers to an alkyl group that contains a heteroatom, while "heterocycloalkyl" reference to a cycloalkyl group that contains a heteroatom. When the term "heteroatom-containing" introduces a list of possible heteroatom-containing groups, it is intended that the term apply to every member of that group.

As illustrated below, the term "fused, tetracyclic" generally refers to a compound that includes four rings therein; and further wherein each of the rings in the compound share two ring atoms (e.g., carbon atoms or heteroatoms, as highlighted by the dashed-circles below). Optionally, when a heteroatom is present, the "fused hetero-tetracyclic" may be used.

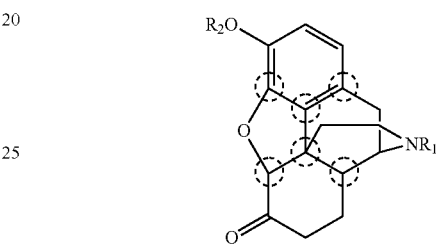

As used here, "structurally related" generally refers to a 6-beta compound that has a structure that is essentially the same as the corresponding compound of Formula VI (e.g., $R_1$, $R_2$, $R_8$, $R_9$, $R_{10}$, $R_{11}$, $R_{14}$, $R_{15}$, $R_{16}$ and $R_{17}$ being the same in both structures), and/or Formula III (e.g., $R_1$, $R_2$, $R_8$, $R_9$, $R_{10}$, $R_{11}$, $R_{14}$, $R_{15}$, $R_{16}$ and $R_{17}$ being the same in both structures).

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

Reaction Kinetics of the Hydrogenation of Thebaine to 8,14-dihydro-thebaine

In this Example, 8,14-dihydro-thebaine was produced by contacting thebaine with p-toluene sulfonyl hydrazide at 80-85° C. using 2-methoxy-ethanol and ethanol-amine, with overhead stirring and a nitrogen purge. The percent conversion of thebaine to 8,14-dihydro-thebaine in the reaction mixture was measured as the reaction proceeded for 390 minutes. The measurements are reported in the graph of FIG. 1.

A portion of the material was worked up using standard extraction and precipitation techniques, and then analyzed by Ultra High Pressure liquid chromatography. Another portion of the material, after cooling and filtering, was similarly analyzed. The solvent-stripped product was 97.5 wt % pure and the filtered product was 95 wt % pure. The 8,14-dihydrothebaine product was white in color.

Example 2

Investigation of the Effect of Varying Temperature in the Hydrolysis of 8,14-dihydro-thebaine to Hydrocodone In this Example, 8,14-dihydro-thebaine was converted to hydrocodone by contacting the 8,14-dihydro-thebaine with concentrated hydrochloric acid at a number of temperatures and reaction times, as detailed in Table C below. The wt % of hydrocodone and the number of impurities in the reaction mixture are also shown in Table C.

TABLE C

Temperature Dependence in the Conversion of 8,14-dihydro-thebaine to hydrocodone.

| Temp (° C.) | % Hydrocodone | Number of Impurities | Total Elapsed Time (min) |
| --- | --- | --- | --- |
| 21.3 | 94.37 | 9 | 100 |
| 40.4 | 92.93 | 10 | 125 |
| 50.3 | 93.80 | 11 | 145 |
| 55.0 | 93.43 | 13 | 170 |
| 65.0 | 93.12 | 14 | 190 |
| 75.4 | 92.51 | 17 | 205 |
| 81.5 | 90.44 | 17 | 225 |
| 79.6 | 84.29 | 29 | 270 |
| 81.3 | 80.68 | 30 | 315 |

In this Example, it was observed that the reaction rate was proportional to the hydrogen ion concentration and equivalency in the reaction mixture. The table shows higher temperatures gave more decomposition products and should be avoided. The Table also shows there is no need for heat; the reaction was complete at room temperature.

Example 3

Production of 8,14-dihydro-thebaine by Hydrogenation of Thebaine and Subsequent Purification Thebaine (142.86 g of 70 wt % material containing 30 wt % water, 100.00 g, 0.321 mol), p-toluene sulfonyl hydrazide (131.58 g, 0.706 mop and ethanol (400 ml) were stirred and heated to 70° C. Ethanol amine (43.16 g, 0.706 mol) was added to this solution over a 1 h period. The reaction was heated for a further 10 h at this temperature and then allowed to cool to room temperature. The reaction was diluted with water (400 ml) and the pH adjusted to >9.30 with concentrated (28.0-30.0%) ammonium hydroxide (30 ml) and cooled to <5° C. The product was isolated by filtration and washed with 1% v/v ammonium hydroxide in water (400 ml) to give 8,14-dihydro-thebaine as a white amorphous solid (91.94 g, 91.3% yield, 99.29 wt % by assay, with 0.16 wt % of the 6-β-parzone methyl ether impurity).

Example 4

Production of Hydrocodone by Hydrolysis of 8,14-dihydro-thebaine using 2.45 N HCl at Room Temperature In this Example, 8,14-dihydro-thebaine (6.00 g, 19.14 mmol) was mixed with 50 ml of approx. 2.45 N hydrochloric acid (122.5 mmol, prepared by mixing concentrated hydrochloric acid (10 ml) with DI water (40 ml)) at room temperature with stirring. The homogeneous light yellow colored solution was stirred overnight. Decolorizing charcoal (Darco, 0.3 g) was added to the mixture and the reaction was stirred for 1 hour and then filtered. The charcoal was washed with DI water (2×5 ml). The combined acid phases were cooled to <5° C. and the pH was adjusted to 9.65 with concentrated (28.0-30.0%) ammonium hydroxide solution (approx. 13 ml). The solid was filtered and washed with 2×5 ml of DI water. The product was dried at 60° C. under 22" Hg vacuum until constant weight to give hydrocodone as a white amorphous solid (5.11 g, 89.2% yield, 96.3 wt % by assay).

Example 5

Production of Hydrocodone by Hydrolysis of 8,14-dihydro-thebaine using 6 N HCl at Room Temperature In this Example, 8,14-dihydro-thebaine (6.00 g, 19.14 mmol) was mixed with 24 ml of approx. 6 N Hydrochloric acid (144 mmol, prepared by mixing concentrated hydrochloric acid (12 ml) with DI water (12 ml)) at room temperature with stirring. The homogeneous light yellow colored solution was stirred for 4 hours. Thin Layer chromatography on silica gel plates 90:10:1 (dichloromethane:methanol: concentrated ammonium hydroxide) indicated that the reaction was complete. Decolorizing charcoal (Darco, 0.3 g) was added to the mixture and the reaction stirred for 20 minutes and then filtered. The charcoal was washed with DI water (2×5 ml). The combined acidic phases were cooled to <5° C. and the pH was adjusted to 9.64 with concentrated (28.0-30.0%) ammonium hydroxide solution (approx. 20 ml). The solid was filtered and washed with 2×10 ml of DI water. The product was dried at 60° C. under 22" Hg vacuum until constant weight to give hydrocodone as a white amorphous said (4.87 g, 84.9% yield, 96.2 wt % by assay).

Example 6

Production of Hydrocodone by Hydrolysis of 8,14-dihydro-thebaine using 12 N HCl at Room Temperature Hydrocodone was prepared according to the process of Example 5; however, 12 N HCl was used rather than 6 N HCl. The reaction was shown to be complete by ultra-high performance chromatography (HPLC) in less than 2 hours without the use of extraneous heat.

Example 7

Production of Hydrocodone by Hydrolysis of 8,14-dihydro-thebaine using 1.8 M Sulfuric Acid at Room Temperature In this Example, 8,14-dihydro-thebaine (6.00 g, 19.14 mmol) was mixed with 20 ml of approx. 1.8 M sulfuric acid (36 mmol, prepared by mixing concentrated sulfuric acid (2 ml of 18 M) with DI water (18 ml) at room temperature with stirring. After 6 hours, the hydrocodone sulfate precipitated out. The mixture was stirred for a further 48 hours. Hydrocodone sulfate penta-hydrate was filtered and washed with 2×5 ml of DI water. The solid was dried at 60° C. under 22" Hg vacuum until constant weight to give hydrocodone sulfate penta-hydrate as a white amorphous sold (2.34 g, 30.9% yield, 100.5 wt % by assay). The remaining acidic phases were combined and cooled to <5° C. and the pH was adjusted to 10.95 with concentrated (28.0-30.0%) ammonium hydroxide solution (approx. 10 ml). The solid was filtered and washed with 2×5 ml of DI water. The product was dried at 60° C. under 22" Hg vacuum until constant weight to give hydrocodone base as an off-white amorphous solid (3.39 g, 59.1% yield, 95.7 wt % by assay).

Example 8

Production of Hydromorphone by Hydrolysis of 8,14-dihydro-oripavine using Concentrated HCl at Room Temperature Initially, 8,14-dihydrooripavine was made in a process analogous to that used for 8,14-dihydrothebaine above (see Examples 1 and 3, above). The 8,14-dihydrooripavine (5.8 g) was then suspended in a solution of 5.8 ml absolute ethanol and 5.8 ml concentrated HCl. The mixture initially had a light yellow color or appearance, and was homogeneous; however, within 2 minutes a white solid formed therein. After 5 minutes, the mixture was analyzed (using thin-layer chromatography) and all of the 8,14-dhihydrothebaine was found to have been consumed.

The reaction was mixed a total of one hour at room temperature. Absolute ethanol (11.6 ml) was added, and then the resulting suspension was cooled to 10° C. and stirred for 1 hour. The solids were collected by filtration, washed with 2×6 ml absolute ethanol, briefly dried in the filter, and then finally dried in a vacuum oven at 50° C. (−22 in Hg). Yield of white solids was 5.80 g (94%).

Example 9

Recrystallization of Hydrocodone Base Containing low 6-β-PME Levels (0.12 wt %)

Hydrocodone crude base (68.24 g, 0.23 mol, 99.16 wt %, with 0.12 wt % 6-β-PME) was heated to 78° C. in 750 ml of ethanol. After 10 minutes at this temperature, the mixture became homogeneous. The homogeneous mixture was concentrated to 400 ml, and then cooled to 5° C. After being held at this temperature for 30 minutes, the mixture was filtered on a Büchner funnel and washed with 50 ml of ethanol. The collected hydrocodone base was a white solid (63.12 g, 92.49%), which had an assay of 99.39 wt % with 0.01 wt % 6-β-PME (a 91.6% purge of the 6-β-PME, as compared to the initial concentration thereof in the crude hydrocodone base).

Example 10

Recrystallization of Hydrocodone Base Containing high 6-β-PME Levels (0.82 wt %)

Hydrocodone crude base (99.09 wt %, with 0.82 wt % 6-β-PME) was recrystallized in a similar fashion to the previous example (Example 9), to obtain a purified hydrocodone base (99.43 wt %, with 0.11 wt % 6-β-PME, which is an 86.5% purge as compared to the initial concentration thereof in the crude hydrocodone base).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A method for preparing a compound of Formula III from a compound of Formula I:

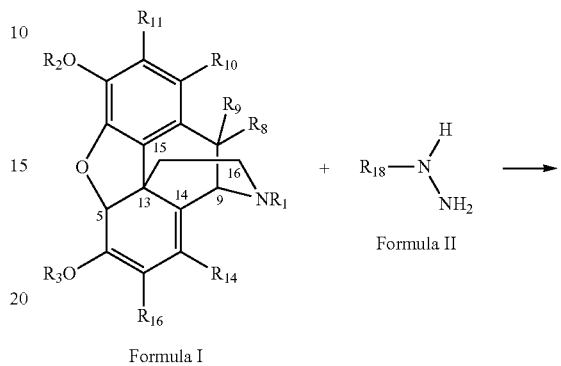

the method comprising contacting the compound of Formula I and a hydrazide reagent of Formula II in a first reaction mixture for at least 6 hours, to convert the compound of Formula I to the compound of Formula III, wherein:

$R_1$ is selected from the group consisting of hydrogen, substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester, and substituted or unsubstituted carboxyamide;

$R_2$ is selected from the group consisting of hydrogen, substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl;

$R_3$ is selected from the group consisting of substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, substituted or unsubstituted heterocycloalkyl;

$R_8$ and $R_9$ are independently selected from the group consisting of hydrogen, hydroxyl, and substituted or unsubstituted hydrocarbyl, or $R_8$ and $R_9$ together form a carbonyl group;

$R_{10}$, $R_{11}$, $R_{14}$ and $R_{15}$ are independently selected from the group consisting of hydrogen, substituted and unsubstituted hydrocarbyl, and a halogen, or $R_{14}$ and $R_{15}$ together form a carbonyl group;

$R_{16}$ is selected from the group consisting of hydrogen, and substituted or unsubstituted hydrocarbyl; and, $R_{18}$ is either an acyl group having the formula $R_{19}$—C(O)— or a sulfonyl group having the formula $R_{20}$—S(O)$_2$—, wherein $R_{19}$ and $R_{20}$ are independently selected from the group consisting of H, substituted or unsubstituted alkyl, substituted or unsubstituted aryl, substituted or unsubstituted aryl alkyl, substituted or unsubstituted cycloalkyl, substituted or unsubstituted heterocycloalkyl, and substituted or unsubstituted heteroaryl.

2. The method of claim 1, wherein the compounds of Formula I and Formula II are contacted for less than about 24 hours in the first reaction mixture.

3. The method of claim 1, wherein the compound of Formula I is converted to the compound of Formula III in the absence of a metal-containing catalyst.

4. The method of claim 1, wherein the first reaction mixture contains the compound of Formula II and the compound of Formula I in a ratio of between about 2:1 and about 4:1.

5. The method of claim 1, wherein the reaction is carried out to convert the compound of Formula IA to the compound of Formula IIIA:

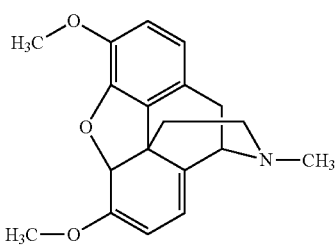

Formula IA

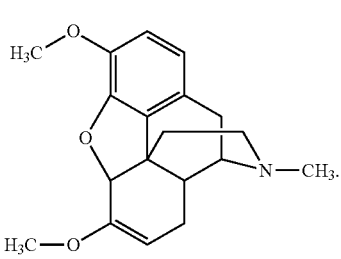

Formula IIIA

6. The method of claim 1, wherein the reaction is carried out to convert the compound of Formula IB to the compound of Formula IIIB:

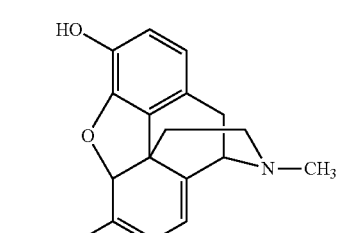

Formula IB

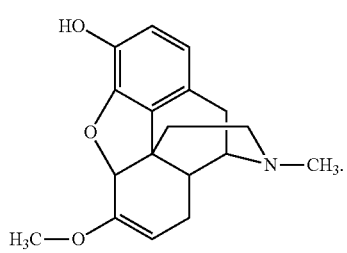

Formula IIIB

7. The method of claim 1, wherein the compound of Formula II is selected from 2,4,6-triisopropylbenzene sulphonyl hydrazide and p-toluene sulphonyl hydrazide.

8. The method of claim 1, further comprising preparing the compound of Formula VI from the compound of Formula III:

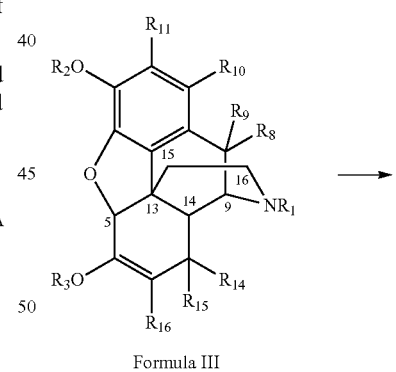

Formula III

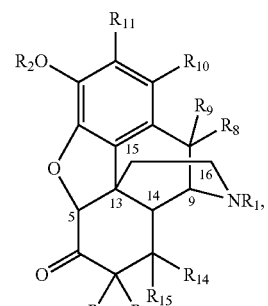

Formula VI the method comprising contacting the compound of Formula III and an acid in a second reaction mixture at a temperature of less than 50° C., to convert the compound of Formula III to the compound of Formula VI, wherein: $R_1$, $R_2$, $R_3$, $R_8$, $R_9$, $R_{10}$, $R_{11}$, $R_{14}$, $R_{15}$, $R_{16}$ are as previously defined in claim 1, and $R_{17}$ is hydrogen.

9. The method of claim 8, wherein the compound of Formula III and the acid are contacted in the second reaction mixture at about room temperature.

10. The method of claim 8, wherein the compound of Formula III and the acid are contacted in the second reaction mixture for between about 0.5 hours and about 3 hours.

11. The method of claim 8, further comprising contacting the compound of Formula VI with a base to give the free base of the compound of Formula VI.

12. The method of claim 8, further comprising recrystallizing the compound of Formula VI to reduce the concentration of an impurity therein having a Formula 6-beta:

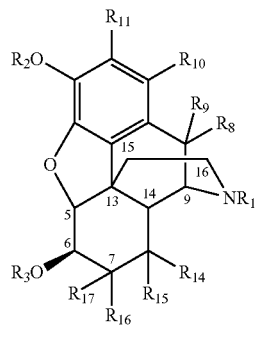

6-beta wherein: $R_1$, $R_2$, $R_3$, $R_8$, $R_9$, $R_{10}$, $R_{11}$, $R_{14}$, $R_{15}$, $R_{16}$ and $R_{17}$ are as previously defined in claim 8, to less than 0.15 wt %.

* * * * *